United States Patent [19]
McKinnis

[11] Patent Number: 6,145,247
[45] Date of Patent: Nov. 14, 2000

[54] FLUID SWITCH

[75] Inventor: Michael K. McKinnis, Chehalis, Wash.

[73] Assignee: Weyerhaeuser Company, Tacoma, Wash.

[21] Appl. No.: 08/883,757

[22] Filed: Jun. 27, 1997

Related U.S. Application Data

[60] Provisional application No. 60/022,001, Jun. 27, 1996.

[51] Int. Cl.$^7$ ............................... A01H 1/00; B03B 5/28; B65G 51/08
[52] U.S. Cl. ............................ 47/57.6; 47/58.1; 209/74; 209/155; 209/509; 406/10; 406/34
[58] Field of Search .................................... 47/58.1, 57.6; 209/74, 155, 509; 406/198, 49, 10, 34

[56] References Cited

U.S. PATENT DOCUMENTS

| | | |
|---|---|---|
| 393,584 | 11/1888 | Robinson . |
| 2,039,016 | 4/1936 | McGuiness et al. . |
| 2,554,583 | 5/1951 | McFall . |
| 2,895,768 | 4/1959 | Bray, Jr. . |
| 3,072,442 | 1/1963 | Ferrari . |
| 3,191,771 | 6/1965 | Odor . |
| 3,536,098 | 10/1970 | Cunningham . |
| 3,560,754 | 2/1971 | Kamentsky . |
| 3,710,933 | 1/1973 | Fulwyler et al. . |
| 3,791,517 | 2/1974 | Friedman . |
| 3,984,307 | 10/1976 | Kamentsky et al. . |
| 4,009,482 | 2/1977 | Nakata . |
| 4,138,089 | 2/1979 | McCarthy . |
| 4,175,662 | 11/1979 | Zold . |
| 4,437,799 | 3/1984 | Liu et al. . |
| 4,442,865 | 4/1984 | Shigeo . |
| 4,715,143 | 12/1987 | Redenbaugh et al. .................... 47/57.6 |
| 4,871,284 | 10/1989 | Duffy . |
| 4,952,099 | 8/1990 | Drobadenko et al. . |
| 5,164,992 | 11/1992 | Turnk et al. . |
| 5,284,765 | 2/1994 | Bryan et al. . |
| 5,316,179 | 5/1994 | Iannoides et al. . |
| 5,427,593 | 6/1995 | Carlson et al. ........................... 47/57.6 |
| 5,564,224 | 10/1996 | Carlson et al. ........................... 47/57.6 |

FOREIGN PATENT DOCUMENTS

| | | |
|---|---|---|
| 0303 472A | 8/1988 | European Pat. Off. . |
| WO 91000781 | 1/1994 | European Pat. Off. . |
| 3336 709A | 4/1984 | Germany . |
| 58104832A | 12/1981 | Japan . |
| 42777125A | 3/1991 | Japan . |

OTHER PUBLICATIONS

Harrell et al., "Machine vision based analysis and harvest of somatic embryos," *Computers and Electronics in Agriculture* 9:13–23, 1993.

Pentland et al., "View–Based and Modular Eigenspaces For Face Recognition," M.I.T. Media Laboratory Perceptual Computing Section Technical Report No. 245, 1994.

Pentland, "Modal Descriptions for Recognition and Tracking," MVA '92, 1 APR Workshop on Machine Vision Applications, Dec. 7–9, 1992, Tokyo.

Pentland, "Experiments With Eigenfaces," M.I.T. Media Laboratory Perceptual Computing Technical Note No. 194, 1992.

Velho, et al., "Density Separation of Zygotic and Somatic Embryos," *Hortscience*, vol. 25(9), Sep. 1990.

*Primary Examiner*—Lynette R. F. Smith
*Assistant Examiner*—Melissa L. Kimball
*Attorney, Agent, or Firm*—Christensen O'Connor Johnson Kindness PLLC

[57] ABSTRACT

The present invention provides apparatus and methods useful, for example, for introducing a desired spacing between or classifying and sorting objects, e.g. plant embryos. Objects carried serially in a fluid stream enter the apparatus via an upstream conduit. A sensor associated with the conduit provides information regarding an object at a particular location in the upstream conduit and produces a signal. A switch coupled to the upstream conduit directs the fluid stream to an appropriate downstream conduit by applying a force to a conduit, e.g., by aligning the upstream conduit with a downstream conduit to create a fluid-tight path. Apparatus according to the present invention are particularly useful for manipulating fragile multicellular biological objects such as plant embryos.

12 Claims, 5 Drawing Sheets

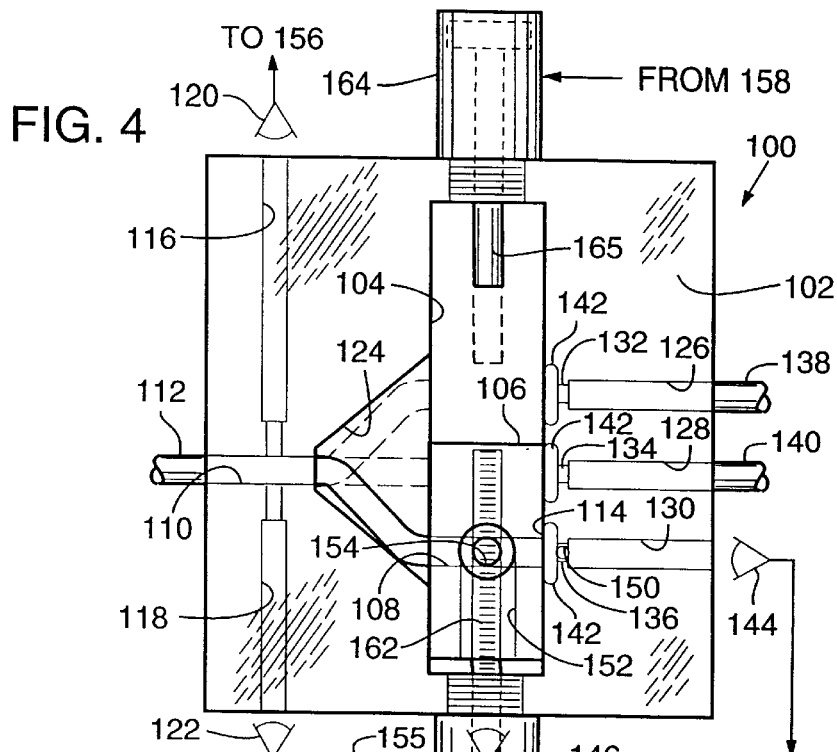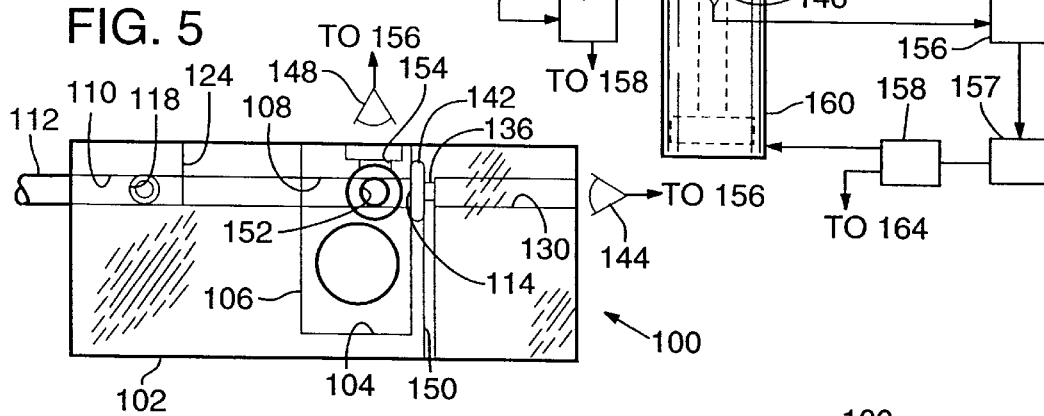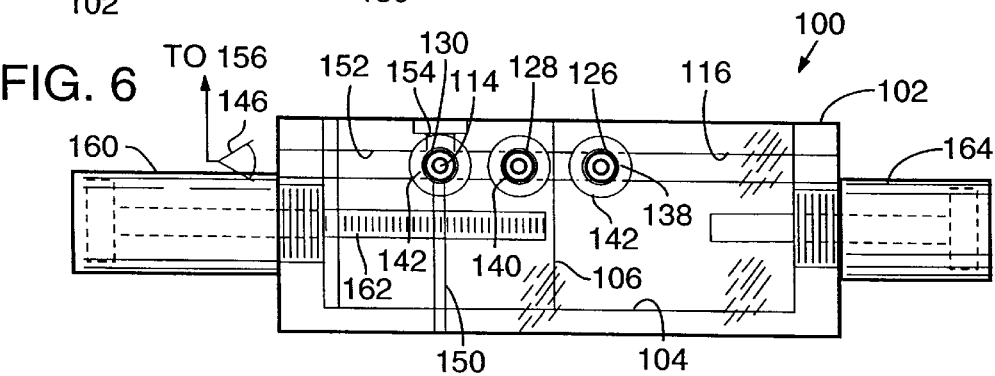

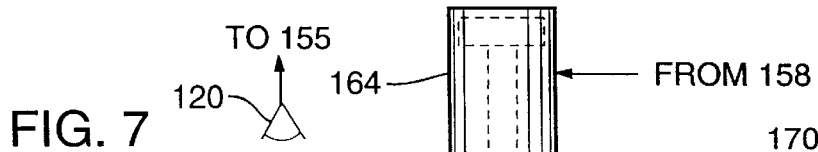

FLUID SWITCH

This application is a Continued Prosecution Application of U.S. patent application Ser. No. 08/883,757, filed Jun. 27, 1997 which is a nonprovisional application based on provisional application No. 60/022,001, filed Jun. 27, 1996.

FIELD OF THE INVENTION

The present invention relates generally to apparatus and methods for automated handling of objects carried in a fluid stream, in particular, to apparatus and methods for sorting living multicellular biological objects such as plant embryos.

BACKGROUND OF THE INVENTION

Modern agriculture often requires the planting of large numbers of substantially identical plants selected to grow optimally in a particular locale or to possess certain other desirable traits. Production of new plants by sexual reproduction, which yields botanic seeds, is a lengthy, labor-intensive process that is often subject to genetic recombinational events resulting in variable traits in the progeny. Furthermore, inbred strains used to perform such crosses often lack vigor, resulting in low seed productivity.

Botanic seeds, such as those produced by conventional plant breeding, have food-storage organs and protective structures that shelter plant embryos from the harsh soil environment, nurture the embryo during sowing and germination, and enable the seed to survive until conditions are favorable for germination.

In view of the disadvantages of producing large numbers of identical progeny plants by sexual means, propagation of commercially valuable plants via culturing of somatic or zygotic plant embryos has been intensively studied. For some species such "asexual" propagation has been shown to yield large numbers of genetically identical embryos, each having the capacity to develop into a normal plant. Unfortunately the resulting embryos lack the protective and nutritive structures found in natural botanic seeds. As a result, the embryos are usually cultured under laboratory conditions until they reach an autotrophic "seedling" state characterized by an ability to produce their own food via photosynthesis, resist desiccation, produce roots able to penetrate soil, and fend off soil microorganisms.

Much effort has been directed to the development of techniques for embryogenesis of agronomically important plant species, including conifer species. See, e.g., U.S. Pat. Nos. 4,957,866, 5,034,326, and 5,036,007. Totipotent plant tissue is developed in culture to a stage similar to the natural zygotic embryos occurring in mature seeds. For conifers, these are very small, commonly ranging from about 2–4 mm in length. Embryos have a bipolar form which anticipates the ultimate plant. One end has a latent radicle or root, and the other end has a latent cotyledon and appears similar to a tiny crown.

Somatic embryos lack the endosperm of the natural seed. In order to provide nutrients to the embryo at the time of germination, somatic embryos may be placed on a solid germination medium that contains the necessary carbohydrate and other nutrients, on a growing medium, or on synthetic soil that is saturated with an appropriate nutrient solution. Sterility must be maintained until after the resulting plantlet is well established. Somatic embryos also lack a seed coat and thus are more susceptible than botanic seed to mechanical damage, desiccation, and attack by pathogens and pests.

A preferred method of germinating a unit of totipotent plant tissue, e.g., a plant somatic embryo, is to incorporate it into a manufactured seed (i.e., "artificial seed" or "seed analog"). A number of versions of manufactured seed have been described in the patent literature, including U.S. Pat. Nos. 4,562,663; 4,583,320; 4,615,141; 4,715,143; 4,777,762; 4,779,376; and 4,780,987 and Canadian Patent No. 1,241,552. More advanced versions of manufactured seed that display an improved germination rate are disclosed in U.S. Pat. Nos. 5,427,593 and 5,236,469, incorporated herein by reference.

Methods and apparatus are needed for producing manufactured seed on a commercial scale. If an economical production rate is to be obtained, this process must be automated as much as possible.

One step in this production of manufactured seed is the selection of totipotent plant tissue, e.g., somatic embryos, that are mature enough to incorporate into manufactured seed. There is typically significant variation in morphological normalcy and embryo maturity in somatic embryos produced by conventional tissue culture methods. Manufactured seed containing morphologically abnormal or immature embryos seldom germinate into normal plantlets. Tedious manual selection has been the standard solution to this problem.

Various apparatus have been described for sorting microscopic biological objects such as single cells. See, U.S. Pat. Nos. 3,560,754, 3,710,933, 3,791,517, 3,987,307, and 4,175,662. These apparatus are generally not useful for sorting larger, multicellular biological objects, particularly macroscopic objects such as plant embryos.

A method has been described for separating loblolly pine zygotic embryos and celery somatic embryos according to maturity criteria using sucrose density gradients (Velho et al., *HortScience,* Programs and Abstracts (suppl.), p. 137, 1989 [Abstract, 87th Annual Meeting of the American Society of Horticultural Science, Tucson, Ariz., Nov. 4–8, 1990]).

U.S. Pat. No. 5,284,765 describes a method of directionally orienting plant embryos in a liquid flotation medium.

Published International Application WO 91/00781 describes the use of a scanner to identify and determine the location of plant embryos and a pipetting mechanism to remove the plant embryos from the liquid culture medium.

Harrell et al., *Computers and Electronics in Agriculture* 9:13–23, 1993, describes a system for classifying plant embryos. Mature embryos are fixed, manually introduced into the system under non-sterile conditions, and optically imaged. Images of the objects are analyzed using a neural network. Objects identified as mature embryos are deflected out of a gap in a conduit in a medium-filled harvest chamber by an injection of culture medium from a control nozzle and collected. Rejected structures pass through the gap and enter a settlement chamber.

There remains a need for automated apparatus and methods for rapidly and efficiently handling multicellular biological objects such as plant embryos under aseptic conditions without subjecting the objects to mechanical forces that would cause substantial damage. In particular, there is a need for apparatus and methods for rapidly separating embryos that are acceptable for producing manufactured seed from unacceptable embryos and delivering the acceptable embryos in an aseptic fluid stream to a location for incorporation into manufactured seed.

SUMMARY OF THE INVENTION

It is an object of the present invention to provide apparatus and methods for introducing a fixed spacing between objects carried in a fluid stream.

It is another object to provide apparatus and methods for classifying objects carried in a fluid stream.

It is another object of the invention to provide apparatus and methods for sorting objects belonging to various classes.

It is another object of the invention to provide apparatus and methods for performing these functions without subjecting fragile biological objects such as plant embryos to mechanical forces, e.g., shear forces, that would damage and reduce the viability of the objects.

It is a further object of the invention to provide such apparatus and methods that maintain an aseptic environment for the biological objects to prevent contamination.

The foregoing objects have been achieved by providing apparatus and methods for directing objects carried serially by a fluid (e.g., a liquid such as water or a culture medium, air, etc.) to a desired destination. The apparatus includes an upstream, or source, fluid conduit and two or more downstream, or destination, fluid conduits. A sensor, e.g., a fiber-optic sensor, is associated with the upstream conduit and provides information regarding objects in the upstream conduit, e.g., the presence of the object at a particular location in the upstream conduit or an image of the object. A switch coupled to the upstream fluid conduit is selectively operable to deliver the fluid stream, and objects carried by the fluid stream, from the upstream conduit to the appropriate downstream conduit.

For example, according to one embodiment of the invention, the switch is selectively operable to apply a force to at least one of the upstream or downstream fluid conduits, e.g., to align an end of an upstream conduit with an end of a downstream conduit according to the information provided by the sensor to produce a single fluid-tight path for the fluid stream and for objects carried therein. Alternatively, the switch comprises a fluid chamber that is selectively operable to be aligned with an upstream conduit to receive the object and then to be moved into alignment with a downstream conduit in order to direct the object thereto.

According to one embodiment of the invention, the upstream conduit is normally connected to a first downstream conduit. A sensor associated with the upstream conduit produces a signal upon detecting the presence of an object at a particular location in the upstream conduit. The switch responds to the signal by delivering the fluid stream to a second downstream conduit. Then, after a predetermined delay, the switch reconnects the upstream conduit with the first downstream conduit. This permits the detected object and a unit volume of the fluid in which the object is carried to enter the second downstream conduit. This embodiment is useful, for example, for automatically achieving a desired spacing between objects that are randomly spaced as they enter the upstream conduit.

According to another embodiment of the invention, the apparatus includes an optical sensor associated with the upstream conduit that produces an image of an object at a particular location in the upstream conduit and transmits the image to a signal processor, which processes the image for display on a monitor for viewing and classification by a human operator, who transmits a signal corresponding with the classification of the object. Alternatively, in an automated apparatus, the signal processor transmits the processed image to a computerized image recognition system that classifies the object and produces a signal corresponding to the classification of the object that causes the switch to direct the object to the appropriate downstream conduit. Apparatus according to the invention are particularly useful for spacing and sorting living biological objects, especially fragile multicellular, macroscopic objects such as plant embryos. The apparatus are designed such that fluid flow is substantially nonturbulent (i.e., laminar) to reduce or eliminate mechanical damage to fragile objects resulting from shear forces. Moreover, the apparatus can be maintained and operated under conditions that maintain asepsis of the medium in which the objects are suspended and prevent contamination of the objects themselves.

The apparatus can be fully automated. Two or more apparatus according to the invention can be arranged in series or in parallel for spacing, orienting, or sorting objects according to multiple criteria. For example, in a commercial process for producing manufactured seed, embryos carried in a fluid stream in a randomly spaced fashion can be directed to one embodiment of the invention to achieve a regular spacing, then directed to another embodiment of the invention in series with the spacing apparatus to classify and sort the embryos and direct embryos that are acceptable for manufactured seed to a location for manufactured seed assembly.

The present invention also provides related methods for directing objects to a desired location, producing a substantially regular spacing between objects, classifying and sorting objects, and producing manufactured seed that include plant embryos sorted by such methods, as well as manufactured seed produced by such methods.

Those skilled in the art will appreciate the utility of this invention which is not limited to the specific experimental modes and materials described herein.

The foregoing and other features and advantages of the invention will become more apparent from the following detailed description and accompanying drawings.

BRIEF DESCRIPTION OF DRAWINGS

FIG. 4 is a top view of a three-position fluid switch according to another embodiment of the invention. The switch is in the third position for viewing purposes, wherein dashed lines indicate the first and second positions.

FIG. 5 is a sectional side view of the fluid switch of FIG. 4.

FIG. 6 is a sectional end view of the fluid switch of FIG. 4.

FIG. 7 is a top view of another embodiment of a three-position fluid switch with a shuttle 172 that is adapted to receive an optical cell 174.

FIG. 8 is a sectional side view of the fluid switch of FIG. 7.

FIG. 9 is a sectional end view of the fluid switch of FIG. 7.

FIG. 10A is an enlarged perspective view of an optical cell.

FIG. 10B is a cross-sectional view of the optical cell of FIG. 10A. The dimensions of the optical cell bore are shown ("a").

DETAILED DESCRIPTION OF THE INVENTION

The following description of various embodiments of apparatus according to the invention discusses use of the apparatus in a process for the production of manufactured seed comprising plant embryos, e.g., for achieving a desired spacing between randomly spaced embryos that are entrained in an aseptic liquid stream (e.g., water or an aqueous plant cell culture medium) or for sorting and separating viable, mature, morphologically normal plant embryos from other objects such as nonviable embryos or non-embryo structures. The invention is not considered limited thereto, however, but would be useful for a variety of purposes, for example, for classifying and separating a wide variety of microscopic or macroscopic living or non-living objects, particularly fragile macroscopic objects.

Figure 1:
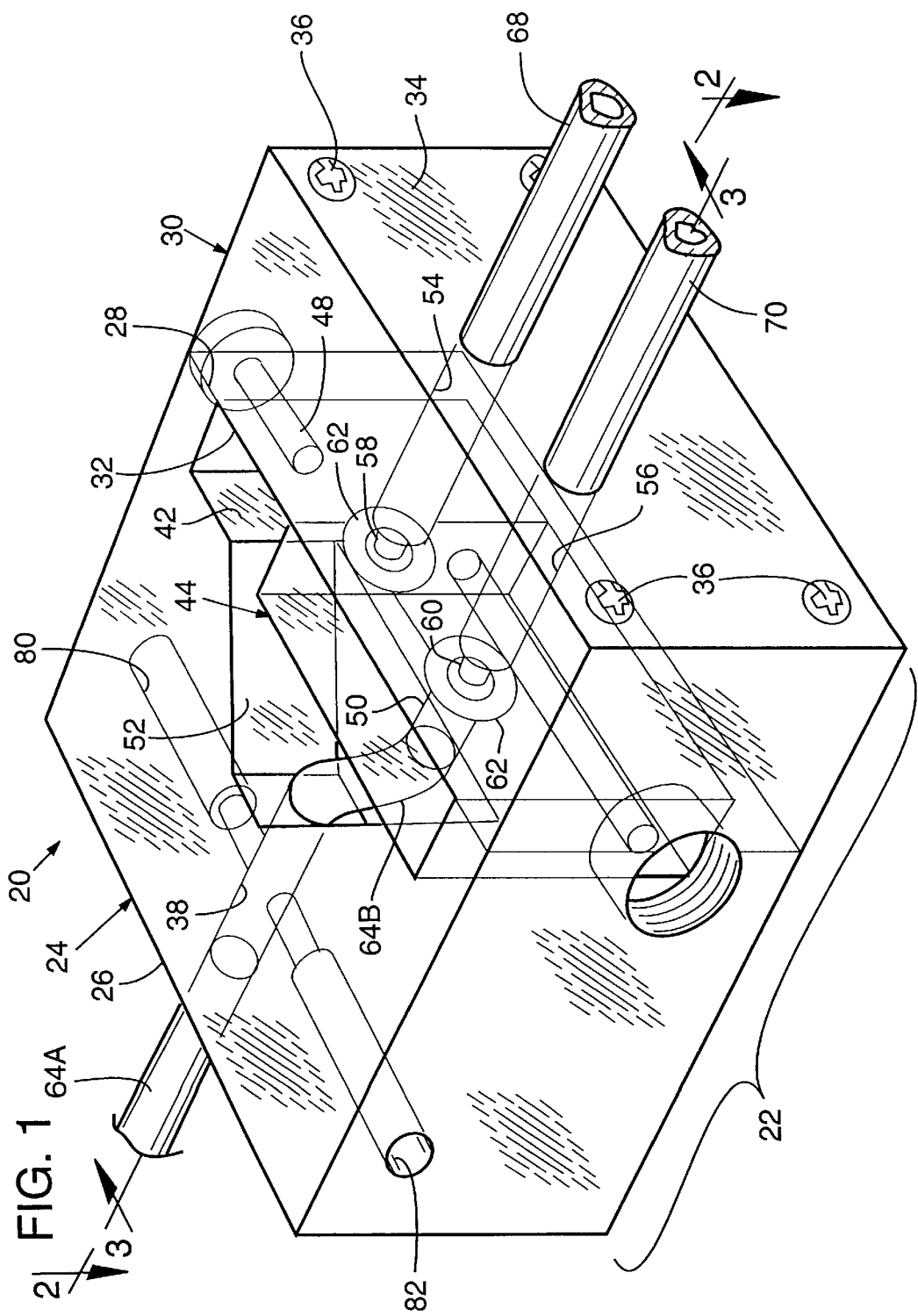
FIG. 1 is a perspective view of a two-position fluid switch according to one embodiment of the invention.
Figure 2:
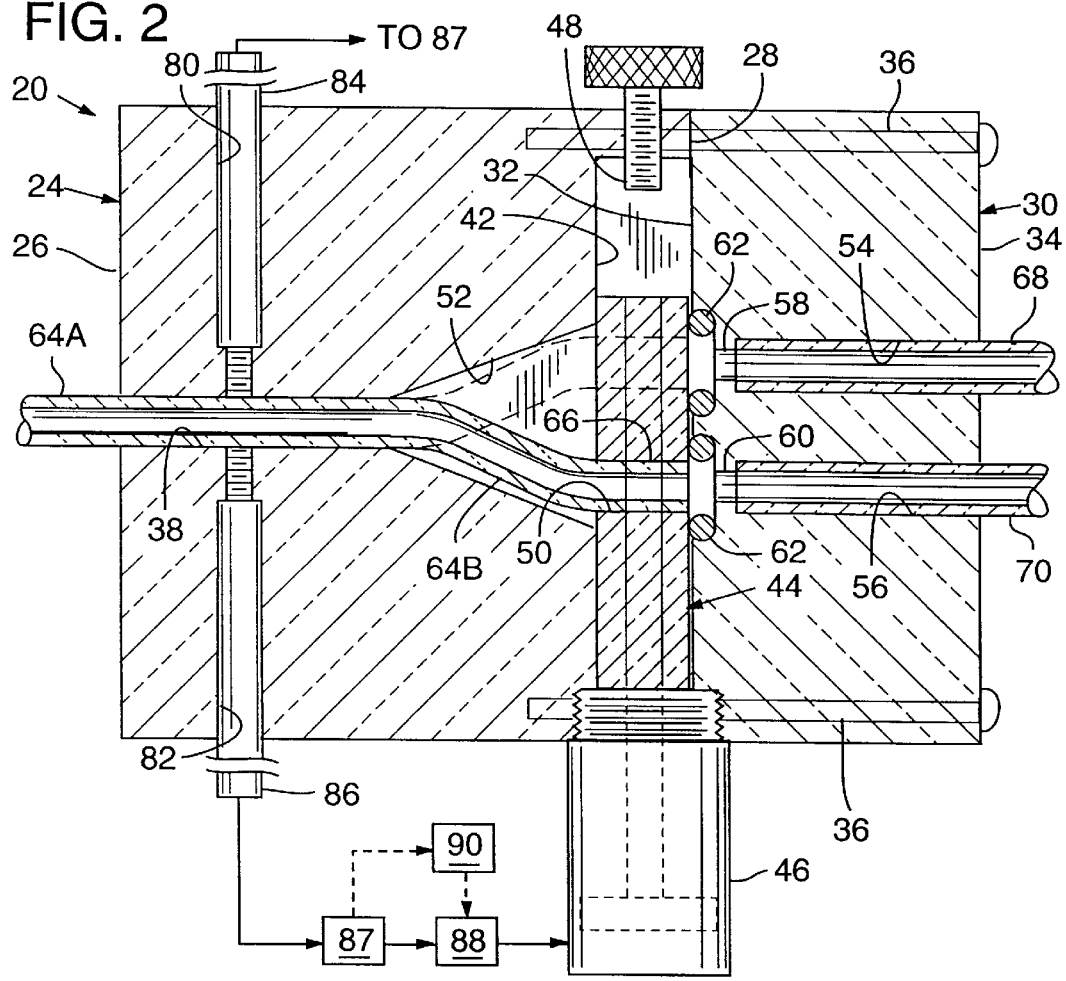
FIG. 2 is a top sectional view of the fluid switch of FIG. 1 in the second position, wherein dashed lines indicate the first position.
Figure 3:
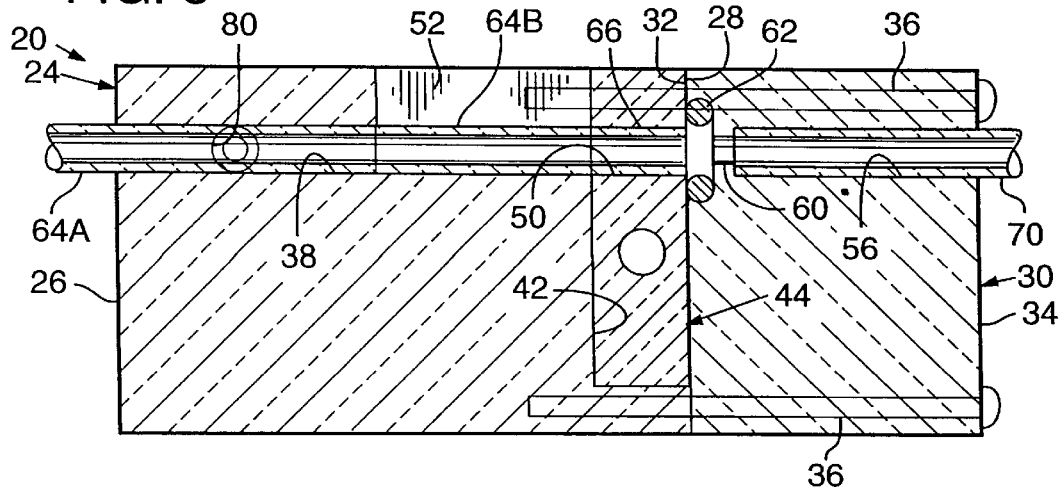
FIG. 3 is a sectional side view of the fluid switch of FIG. 1.

FIGS. 1–3 show a two-position fluid switch 20 according to the invention. The fluid switch 20 comprises a body 22 that includes an upstream body portion 24 having an upstream end 26 and a downstream end 28 and an adjacent downstream body portion 30 having an upstream end 32 and a downstream end 34. The downstream body portion 30 is preferably mounted to the upstream body portion 24 with screws 36. An upstream bore 38 is defined by and extends into upstream body portion 24.

A shuttle cavity 42 is also defined by the upstream body portion 24 adjacent the downstream body portion 30. A slide, or shuttle, 44 is slidably disposed in the shuttle cavity 42. The shuttle 44 dimensionally conforms to the shuttle cavity 42 to allow the shuttle 44 to be moved back and forth in the shuttle cavity 42 by an actuator 46, such as a standard two-way pneumatic positioning cylinder that is attached to one end of the shuttle 44. A wide variety of conventional actuators can be employed. A calibration stop post 48 threadably extending through the upstream body portion 24 and into the shuttle cavity 42 provides an adjustable stop for the shuttle 44. A cylindrical shuttle bore 50, preferably having substantially the same diameter as the upstream bore 38, is defined in the shuttle 44. The shuttle bore 50 can be axially aligned with the upstream bore 38 or can be displaced a distance to either side of the upstream bore 38 by side-to-side movement of the shuttle 44 in the shuttle cavity 42.

As shown in FIGS. 1–3, the downstream body portion 30 defines spaced-apart nonintersecting first and second downstream bores 54, 56, respectively, preferably having substantially the same diameter as the upstream bore 38. The downstream bores 54, 56 each have a corresponding open upstream end 58, 60, respectively. Surrounding each upstream end 58, 60 is a respective gland adapted to receive a silicone O-ring 62 to provide a liquid-tight seal between the upstream ends 58, 60 and the shuttle 44. The O-rings are preferably made of silicone rubber or other suitable material.

The downstream bores 54, 56 are equilaterally spaced apart from each other on opposite sides of an axis defined by the upstream bore 38 and are substantially coplanar with the upstream bore 38 and the shuttle bore 50. The length of the shuttle 44 and the positions of the downstream bores 54, 56 are such that the shuttle bore 50 can be aligned with either of the downstream bores 54, 56.

An aseptic upstream conduit 64A, e.g., a length of a flexible transparent tubing (e.g., Tygon® tubing, Norton Co.), is coaxially connected to the upstream bore 38 to deliver objects entrained in a fluid stream, e.g., biological objects such as plant embryos, to the shuttle 44. An aseptic flexible conduit 64B is also axially connected to the upstream bore 38 and the shuttle bore 50 to deliver fluid-entrained objects through the shuttle 44. For plant embryos, the fluid is preferably water or an aqueous culture medium, although for other objects, air or another fluid can be employed.

The upstream conduit 64 preferably has an inner diameter that is greater than that of the diameter of objects entrained in the liquid stream but small enough to ensure that the objects pass through the fluid switch 20 serially (e.g., about one-eighth inch in diameter for conifer embryos). The upstream conduit 64 has an open downstream end 66 (FIG. 2) that is flush with the surface of the shuttle 44 adjacent the upstream end of the downstream body portion 32.

First and second downstream conduits 68, 70 (which may be either flexible or inflexible, and which may be transparent or non-transparent) are disposed within the first and second downstream bores 54, 56, respectively, in the downstream body portion 30. The upstream opening 58, 60 of each of the first and second downstream bores preferably has a diameter substantially equal to the inside diameter of the upstream and downstream conduits.

As it moves reciprocatively in the shuttle cavity 42, the shuttle 44 carries the upstream conduit 64B with it. Free lateral movement of the upstream conduit 64B is facilitated by a V-shaped void 52 defined by the upstream body portion 24. In this way, the downstream end 66 of the upstream conduit 64B can be aligned with either the upstream end 58 of the first downstream bore ("first position") or the upstream end 60 of the second downstream bore ("second position"), respectively, to provide a single, continuous pathway for the movement of the fluid stream and objects carried by the fluid stream through the fluid switch 20. The O-rings 62 provide a fluid-tight seal between the downstream end of the upstream conduit 66 and an upstream opening 58 or 60 of a downstream bore or between the downstream end 66 of the upstream conduit and the upstream end 32 of the downstream body portion when the shuttle is moving between the first and second positions. Thus, the fluid path through the switch is fluid-tight, i.e., both fluid leakage and contamination of the fluid and objects carried therein is prevented.

The upstream sensor bores 80, 82 are aligned on opposite sides of and horizontally intersect the upstream bore 38. Sensors 84, 86 that are suitable for detecting the presence of an object in the upstream conduit (e.g., a light-path or ultrasonic sensor, such as a FS2 series color mark fiber sensor, model FU-75, Keyence Corp., Osaka, Japan) are disposed in the upstream sensor bores 80, 82 (one sensor serving as a light or ultrasonic transmitter, the other sensor serving as a receiver).

Upon detection of an object in the upstream conduit 64A, the upstream sensors 84, 86 transmit a signal to a signal processor 87. The signal processor processes the signal and transmits a processed signal to a programmable logic controller 88 (PLC, e.g., model KX-10R(T), Keyence Corp., Osaka, Japan) that includes the appropriate switching logic (preferably electrical or pneumatic) and drive circuitry to control the actuator 46, which moves the shuttle 44 to a desired position.

The fluid switch 20 can be used, for example, to achieve a substantially regular spacing between embryos entrained in a liquid stream. The shuttle 44 is maintained in the second position until an embryo is detected by upstream sensors 84, 86, which transmit a signal to the signal processor 87, which processes the signal and transmits the processed signal to the controller 88. After an appropriate delay, the controller 88 causes the actuator 46 to move the shuttle 44 to the first position. After a preset delay, controller 88 causes actuator 46 to move shuttle 44 back to the second position, thereby establishing a predetermined gap or spacing between embryos in the first downstream conduit 68. Water is discharged through the second downstream conduit 70 to be recycled until another embryo is sensed by the upstream sensors 84, 86.

Such a two-position fluid switch 20 can also be used to classify and separate normal embryos from other objects (e.g., immature embryos, morphologically abnormal embryo structures, debris, etc.) that are spaced apart in a liquid stream. After an object enters the fluid switch 20 via the upstream conduit 64A, the upstream sensors 84, 86 (e.g., standard fiber optics borescopes, such as models A8-260-F45 or A8-260-R45, Genesys Instruments, Inc.) generate images of the object and transmit the images to a signal processor 87, which in turn transmits a processed signal to a monitor 90a. A human operator views the monitor and classifies the object as a normal embryo ("accept") or other object ("reject"). Based on the classification, the operator sends a signal to the controller 88, which causes the actuator 46 to move the shuttle 44 to the appropriate position. If the object is classified as a normal embryo, the shuttle 44 is moved to the first ("accept") position to permit the embryo to continue to a location for incorporation into manufactured seed. If an object is classified as a non-embryo, the shuttle 44 is moved to the second ("reject") position to permit the non-embryo to continue to a waste receptacle or other desired destination (or vice versa). A delay can be introduced between classification of the object and movement of the shuttle. In an alternate embodiment, the monitor 90a (and human operator) is replaced with a computerized image processor 90b, which automatically analyzes and classifies the object on the basis of the processed signal received from the signal processor 87 and transmits a signal according to the classification to the controller 88.

As shown, the upstream conduit 38 is coupled to only one of the downstream conduits 54 or 56 at a time to create a single enclosed fluid path for the object. Moreover, neither of the downstream conduits need intersect with the upstream bore, permitting a connection to be formed between a single upstream fluid conduit and three or more downstream fluid conduits, if desired, as is exemplified below.

Three-Position Fluid Switch

One embodiment of a three-position fluid switch 100 according to the present invention is shown in FIGS. 4–6. The body 102 of the fluid switch (shown for the sake of simplicity as a one-piece body in FIGS. 4–6, although a two-piece body as shown in FIGS. 1–3 can be used) defines a shuttle cavity 104. A shuttle 106 defining a shuttle bore 108 is disposed in the shuttle cavity 104. The body 102 also defines an upstream bore 110. A flexible, transparent upstream conduit 112 is disposed within and coaxially connected to the upstream bore 110 and has an open downstream end 114 inserted in the shuttle bore 108. The body 102 also defines upstream sensor bores 116, 118 corresponding to upstream optical sensors 120, 122 (shown in FIG. 4 as "eye" symbols) to detect the presence of an object in the upstream conduit 112. The body 102 also defines a V-shaped void 124 for unhindered movement of the upstream conduit 112 by the shuttle 106. These elements are similar in design and function to analogous elements of the two-position fluid switch described above.

Spaced apart, parallel first, second, and third downstream bores 126, 128, and 130, respectively, having corresponding open upstream ends 132, 134, 136 are defined by the body 102. First and second downstream conduits 138, 140 (which need not be flexible or transparent), are disposed in the corresponding first and second downstream bores 126, 128.

The shuttle 106 is reciprocally slidable to align the open downstream end 114 of the upstream conduit 112 with the open end 132 of the first downstream bore ("first position"), the open end of the second downstream bore 134 ("second position"), or open end 136 of the third downstream bore ("third" or "viewing position"). O-rings 142 provide a liquid seal between the downstream end 114 of the upstream conduit 112 and any of the upstream openings 132, 134, 136 of a downstream bore when the shuttle 106 is so aligned or between the downstream end 114 of the upstream conduit and the shuttle cavity 104 to prevent leakage when the shuttle 106 is moving between these positions.

As shown in FIGS. 4–6, the fluid switch 100 includes a vision system that includes three downstream optical sensors (e.g., borescopes) 144, 146, 148 (shown in FIGS. 4–6 as eye symbols), that are oriented to produce images of an object located in the upstream conduit 112 in the shuttle bore 108 from three views. The sensor 144 provides a horizontal view in an upstream direction along an axis defined by the third downstream bore 130. The sensor 144 is disposed in and closes the third downstream bore 130 downstream of a fluid bleed channel 150, by means of which fluid can exit the system or be recycled. The sensor 144 is stationary during operation of the fluid switch 100. The sensor 146 is positioned in the sensor bore 152 to provide a second horizontal view along the long axis of the shuttle 106 and can be either stationary during operation of the fluid switch 100 or attached to and move with the shuttle 106. The sensor 148 is positioned in the sensor bore 154 to provide a third view vertically downward at substantially a right angle to the shuttle bore 108 when the switch 100 is in the third position. The sensor 148, like the sensor 146, can be either stationary during operation of the switch 100 or be attached to and move back and forth with the shuttle 106. The sensors 144, 146, and 148 are positioned such that the viewing end of each sensor is proximate the shuttle bore 108 when the switch 100 is in the third position, so as to provide images of an object in the shuttle bore with a minimum of distortion.

A programmable logic controller 158 controls the positioning of the shuttle 106 by a first actuator 160, e.g., a two-way pneumatic cylinder that is attached to the shuttle 106 by a threaded rod 162, and a second, opposing, two-way pneumatic cylinder 164 that limits the travel of the shuttle 106 by means of rod 165.

In use, a normal embryo or other object entrained in a liquid stream enters fluid switch 100 via the upstream conduit 112 and moves past upstream sensors 120, 122. Upon detection of an object at a particular location in the upstream conduit, the upstream sensors 120, 122 send a signal (such as an object image) to a signal processor 155, which processes the signal and transmits the processed signal to the controller 158. After a preset delay, the controller 158 signals actuators 160, 164 to move the shuttle 106 to the third position. The object enters the shuttle bore 108, displacing fluid through the fluid bleed channel 150. The controller 158 then signals a fluid flow control means (e.g., a pump or valve upstream of the fluid switch 100 or a valve downstream of the fluid bleed channel 150) to stop fluid flow, thereby maintaining the position of the object in the shuttle bore 108 at a position suitable for the downstream sensors 144, 146, 148 to generate images of the object. The object images are processed by a conventional signal processor 156 and transmitted to a conventional monitor 157a for viewing and classification by a human operator, or, in an alternate embodiment, transmitted to a computerized image processing system 157b for analysis and classification. The human operator or image processing system 157b transmits a signal corresponding to the classification to the controller 158, which causes the actuators 160, 164 to move the shuttle 106 to the corresponding first or second position, permitting the object to continue into the first or second downstream conduit 138, 140, respectively. After a preset delay to permit the object to move a distance downstream of the shuttle 106, the controller 106 causes the actuators 160 and 164 to return the shuttle 106 to the third position.

As shown in FIGS. 4–6, the downstream sensors 144, 146, 148 provide orthogonal views of the object. However, the downstream sensors 146 and 148 can be disposed at various angles, e.g., downstream sensor 144 can be oriented as shown to provide an end-on view of the object, with downstream sensors 146 and 148 oriented at a right angle with respect to downstream sensor 144 and at a 60-degree angle with respect to each other.

Another embodiment of a three-position switch 170 is shown in FIGS. 7–10. The shuttle 172 is adapted to receive an optical cell 174 (shown in enlarged views in FIGS. 10A and 10B). The bore 176 of the optical cell 174 has a square cross-section with interior dimensions ("a" in FIG. 10B) that are substantially the same as the interior diameters of the upstream conduit 178 and the first and second downstream conduits 180 and 182, respectively. The sensor 184 is disposed in the third downstream bore 190 and is stationary during operation of the switch 170. The sensor 186 is disposed in the sensor bore 192 and can be either stationary during operation of the switch 170 or attached to and move with the shuttle 172. The sensor 188 is in a vertical orientation so as to view an object through the sensor bore 194 and, like the sensor 186, can be either stationary during operation of the switch 170 or be attached to and move with the shuttle 172. The sensors 184, 186 and 188 are positioned such that the viewing end of each sensor is proximate the optical cell 174 when the switch 170 is in the third position so as to provide images of an object in the optical cell bore 176 with a minimum of distortion. Gaps between the surface of the optical cell 174 and the sensors 186, 188 can be reduced by disposing a lens or optical flat of an optically clear material (not shown) in contact with a surface of the optical cell 174 at the end of sensor bores 192 and 194 (in sensor bore 194, such a lens or optical flat is preferably coplanar with the surface of the shuttle 172) to reduce light reflection and distortion of object images. The switch 170 is otherwise similar in construction and operation to the three-position switch 100 shown in FIGS. 4–6.

The optical cell 174 is preferably made of an optically clear material (e.g., an optical-grade plastic or glass) to reduce optical distortion of object images produced by the downstream sensors 184, 186 and 188. The flat interior surfaces of the optical cell bore 176 are also intended to reduce optical distortion of object images in the optical cell bore 176 that are produced by the downstream sensors 186 and 188. (Alternatively, if the optical cell 174 has a cylindrical bore, images of an object in the optical cell 174 that are obtained by downstream sensors 186 and 188 through the curved surface of the optical cell bore can be corrected by an appropriate cylindrical lens.)

Three-Position Fluid Switch with Rotary Shuttle

Figure 11:
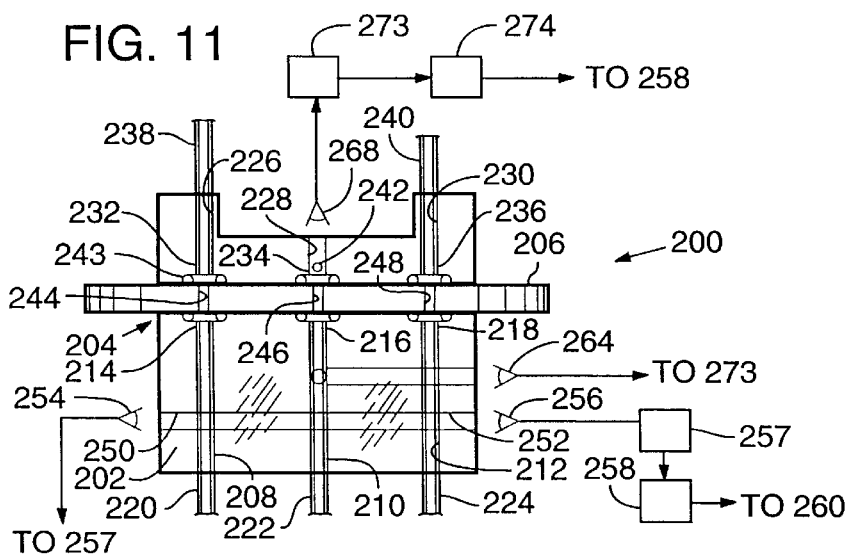
FIG. 11 is a top view of a three-position fluid switch with a rotary shuttle according to another embodiment of the invention.
Figure 12:
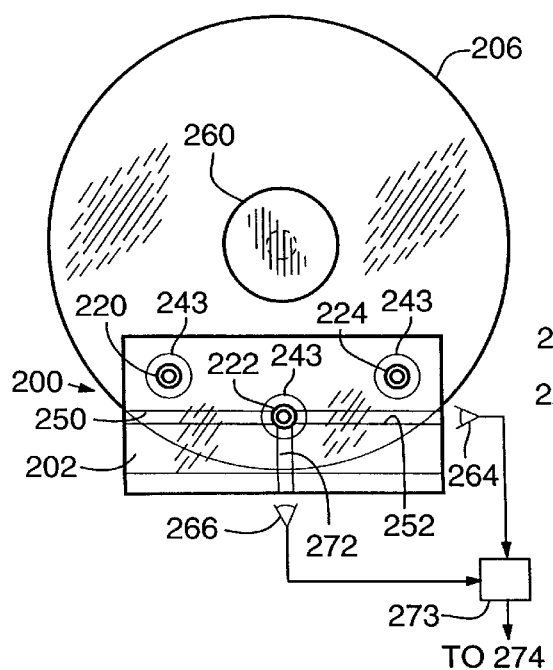
FIG. 12 is a side view of the fluid switch of FIG. 11.
Figure 13:
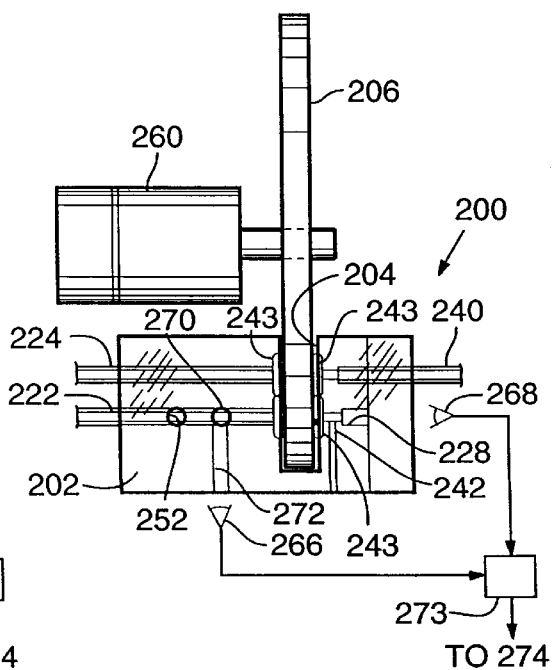
FIG. 13 is an end view of the fluid switch of FIG. 11 including a servo motor for selectively rotating the rotary shuttle.

An alternative embodiment including a rotary shuttle is shown in FIGS. 11–13. The fluid switch 200 has a body 202 (shown as a one-piece body) defining a shuttle cavity 204, in which is disposed a disk-shaped rotary shuttle 206 having a thickness slightly less than the width of the shuttle cavity 204.

The body 202 defines first, second, and third upstream bores 208, 210, 212, respectively, upstream of the shuttle cavity 202. The upstream bores have corresponding open downstream ends 214, 216, 218. In the upstream bores are disposed corresponding first, second and third upstream conduits 220, 222, 224.

The body 202 also defines first, second, and third downstream bores 226, 228, 230, respectively, downstream of the shuttle cavity 204. The downstream bores 226, 228, 230 have corresponding open upstream ends 232, 234, 236. The downstream conduits 238, 240 are disposed in the first downstream bore 226 and the third downstream bore 230, respectively. No conduit need be disposed in the second downstream bore 228, which may therefore have a different diameter than the first and third downstream bores, 226, 230, respectively. A fluid bleed channel 242 is connected to the second downstream bore 228 close to the upstream end 234. An O-ring 243 is disposed in a gland around each of the open ends 232, 234, 236 to provide a liquid seal between the open end and the shuttle 206.

The shuttle 206 defines first, second, and third shuttle bores 244, 246, 248, respectively, each having a diameter substantially the same as the inside diameter of the upstream and downstream conduits.

The upstream, downstream, and shuttle bores are spaced apart and lie on an arcuate plane such that corresponding upstream, downstream, and shuttle bores can be aligned as shown in FIGS. 7–9. The shuttle can be rotated such that the second shuttle bore 246 is selectively aligned with any one of the downstream bores.

Adjacent the second upstream bore 210 are upstream sensor bores 250, 252 in which are disposed upstream optical sensors 254, 256, respectively (shown in FIGS. 11–13 as eye symbols). Upon detection of an object in the second upstream conduit 222, the upstream sensors 254, 256 transmit a signal to a signal processor 257, which in turns transmits a signal to controller 258. The controller 258 controls rotation of the shuttle 206 via a servo stepper motor 260 or analogous actuator.

Unlike the two-position fluid switch 20 and three-position fluid switches 100 and 170 described above, the shuttle 206 in the three-position switch 200 does not carry the end of an upstream conduit. As a result, the upstream and downstream conduits need not be flexible. At least the second upstream conduit 222 is preferably transparent.

The fluid switch 200 also includes an imaging system that includes three optical sensors 264, 266, 268 (shown in FIGS. 11–13 as eye symbols). The first optical sensor 264 is disposed in a sensor bore 270 that horizontally intersects the second upstream bore 210 at about a right angle. The second optical sensor 266 is disposed in a sensor bore 272 that vertically intersects the second upstream bore 210. All three optical sensors 264, 266, 268 are stationary during operation of the fluid switch 200. As shown in FIGS. 11–13, sensor bores 270, 272 and respective sensors 264, 266 disposed therein are oriented at approximately right angles to each other to provide orthogonal views of an object in the upstream bore 210. The third optical sensor 268 is disposed in and closes the second downstream bore 228 to provide a view of an object upstream along the axis defined by the second upstream bore 210 and the second downstream bore 228. Thus, the three optical sensors 264, 266, 268 provide views of an object along three intersecting axes. As discussed above, the angle along which the object is viewed by the downstream sensors can be varied.

The sensors 264, 266, 268 generate images of an object and transmit the images to a conventional signal processor 273 to convert the object images into a form suitable for a conventional monitor 274a for viewing and classification by a human operator, or, in an alternate embodiment, for analysis and classification by a computerized image processing system 274b. The human operator viewing monitor 274a or the image processing system 274b then sends a signal corresponding to the classification to the controller 258. The controller 258 controls rotation of shuttle 206 via a servo stepper motor 260 (the support bracket for the motor 260 is not shown).

In use, the upstream sensors 254, 256 detect an object in the second upstream conduit 222 and transmit a signal to the signal processor 257, which processes the signal and transmits the processed signal to the controller 258. After a preset delay, the controller 258 stops fluid flow in the second upstream conduit 222, and thus the movement of the object carried by the liquid in the upstream conduit 222, to permit viewing of the object by the sensors 264, 266 (i.e., at the "first viewing position"). The sensors 264, 266 generate images of the object, which are processed by signal processor 273 and transmitted to the monitor 274a to be viewed and analyzed by a human operator, who classifies the object (accept/reject) and sends a signal to the controller 258 corresponding to the classification. Alternatively, a computerized image processing system 274b analyzes and classifies the object on the basis of the processed image received from the signal processor 273 and sends an appropriate signal based on the object classification to the controller 258. The controller 258 stops fluid flow in the second upstream conduit 222 by signalling the motor 260 to rotate the shuttle 206 to a position at which the shuttle 206 blocks the flow of liquid and entrained objects. Alternatively, the controller 258 can stop fluid flow in the second upstream conduit 222 by signalling a fluid flow control means (e.g., a pump or valve) upstream of the fluid switch 200 or, when the shuttle 206 is in the second position, by signalling a fluid flow control means such as a valve downstream of the fluid bleed channel 242.

If a reject decision is made, an appropriate signal is sent to the controller 258, which causes the motor 260 to rotate the shuttle 206 until the downstream end 216 of the second upstream bore 210, the second shuttle bore 246, and the upstream end 234 of the second downstream bore are aligned ("second position"). The object enters the second shuttle bore 246 and liquid is pushed into the fluid bleed channel 242. Then, after a preset delay to permit the object to enter the second shuttle bore 246, the shuttle 206 is rotated until the second shuttle bore 246 is aligned with the downstream end 214 of the first upstream bore 208 and the upstream end 232 of the first downstream bore 226 ("first" or "reject position"). (If desired, after a preset delay to allow the embryo to enter the second shuttle bore 246 and before the shuttle 206 is rotated to the first position, fluid flow in the second upstream conduit 222 can be stopped as described above). After a preset delay to allow the rejected object to be pushed by purge liquid from the first upstream conduit 220 into the downstream conduit 238, the controller 258 signals the motor 260 to rotate the shuttle 206 back to the second position to begin the next cycle (if necessary, the controller 258 also signals the fluid flow control means to resume fluid flow.) The rejected object eventually continues to an appropriate destination, e.g., a waste receptacle. The second shuttle bore 246 thus serves: first, as a portion of a continuous, enclosed fluid-tight path that includes the second upstream conduit 222, the second shuttle bore 246, and the second downstream bore 228; second, as a fluid chamber to receive the embryo (and a volume of fluid) and deliver the embryo to an appropriate downstream fluid conduit, in this instance, the downstream conduit 238; and third, as part of a second fluid-tight path, in this case including the first upstream conduit 220, the second shuttle bore 246, and the downstream conduit 238.

If an accept decision is made, the shuttle 206 is rotated to the second position. After a preset delay to permit the object to enter the second shuttle bore 246, the controller 258 stops fluid flow in the second upstream conduit 222 to maintain the position of the embryo in the second shuttle bore 246 ("second viewing position"). The third sensor 268 then generates additional images of the object that are transmitted to the monitor 274 and analyzed by the human operator, who again classifies the object (accept/reject).

Once this second classification is complete, an appropriate accept or reject signal is sent to the controller 258. If the object is rejected, the shuttle 206 is rotated to the reject position and the object is pushed into the downstream conduit 238, as discussed above. If the object is accepted as a normal, mature embryo, the shuttle 206 is rotated until the second shuttle bore 246 is aligned with the downstream end 218 of the third upstream bore 212 and the upstream end 236 of the third downstream bore 230 ("third" or "accept position"). In this position, purge liquid from the third upstream conduit 224 pushes the embryo into the downstream conduit 240. Eventually the embryo continues to a location for incorporation into manufactured seed. Thus, the fluid switch 200 employs a two-stage process of classification and sorting instead of the one-stage classification and sorting process described above for the three-position fluid switch 100.

The above-described fluid switches 20, 100, and 200, including the bodies and shuttles thereof, can be made of a variety of materials, e.g., plastic materials (including opaque plastics such as Delrin® or clear plastics such as acrylics, including plexiglass), metals (e.g., food-grade stainless steel), ceramics, etc., preferably non-phytotoxic, food grade materials that can be sterilized by standard techniques. For production of high quality images of objects, it is preferable that at least the shuttle be made of an opaque, non-reflective material, such as black Delrin®.

It will be readily appreciated by those of ordinary skill in the art that the above-described embodiments of the present invention can be modified, for example, to couple multiple upstream conduits to one downstream conduit or to multiple downstream conduits.

Although embodiments of the invention are described above in terms of a shuttle moving the downstream end of the upstream conduit into alignment with the upstream end of a downstream fluid conduit, in alternative embodiments the upstream end of a downstream fluid conduit can be moved into alignment with the downstream end of an upstream fluid conduit. In such an embodiment of the invention, the upstream conduit could be inflexible and stationary.

Classification of Objects

Features for distinguishing morphologically normal, mature embryos from "non-embryos" (including immature embryos, morphologically abnormal embryos, and non-embryo structures such as debris) include but are not limited to: size characteristics, e.g., length and diameter; shape characteristics, e.g., circularity, symmetry, and elongation; surface characteristics, e.g., roughness, etc.; the presence, size, and normalcy of anatomical features, e.g. cotyledons (see, e.g., Buchholz and Stimert, *Ill. Acad. Sci. Trans.* 38:27–50, 1945); and so on. Images of objects generated by optical imaging systems (including borescopes as discussed above), for example, can be readily and automatically analyzed by object-recognition software. Currently available software can be used or readily adapted for use in classifying objects such as plant embryos on the basis of various characteristics, including, but not limited to, those listed above.

Methods of Producing Manufactured Seed

A number of versions of manufactured seed and methods for their production have been described in the patent literature, including U.S. Pat. Nos. 4,562,663; 4,583,320; 4,615,141; 4,715,143; 4,777,762; 4,779,376; and 4,780,987 and Canadian Patent No. 1,241,552. More advanced versions of manufactured seed that display an improved germination rate are disclosed in U.S. Pat. Nos. 5,427,593 and 5,236,469, incorporated herein by reference.

Fluid switches according to the present invention are particularly well suited for automated methods useful in a commercial process of producing manufactured seed. Plant embryos are first directionally oriented and introduced into a flowing liquid stream into a conduit, preferably without the need for human manipulation, e.g., as described in U.S. Pat. No. 5,284,765, incorporated herein by reference. A substantially regular spacing between the embryos is achieved employing a fluid switch according to the present invention, as described above. Next, normal, mature embryos having a high probability of germinating and developing into normal plants are separated from other objects such as immature or morphologically abnormal embryos and non-embryo structures by means of a fluid switch according to an embodiment of the invention and delivered to an assembly location for incorporation into a manufactured seed.

Briefly stated, to assemble one embodiment of a manufactured seed, a unit of totipotent plant tissue is disposed relative to a hydrated gel so as to permit liquid transfer from the gel to the embryo. At least the shoot (or cotyledon) end of the plant tissue is enclosed by a shoot restraint, which is adapted to resist penetration by the shoot upon germination, to permit access of the plant tissue to gases and liquids, and to be shed distally off the shoot during germination. The plant tissue, gel, and shoot restraint are enclosed within a substantially rigid capsule. The capsule (or manufactured seed coat) protects the plant tissue from mechanical damage, desiccation, and pathogens and pests when the manufactured seed is placed on or in soil.

All publications and published patent documents cited in this specification are incorporated herein by reference to the same extent as if each individual publication or patent application was specifically and individually indicated to be incorporated by reference.

Having illustrated and described the principles of the present invention, it should be apparent to persons skilled in the art that the invention can be modified in arrangement and detail without departing from such principles. We claim all modifications that are within the spirit and scope of the appended claims.

What is claimed is:

1. A method for directing plant embryos from a first upstream fluid conduit to one of at least two downstream fluid conduits, the method comprising:

(a) transporting plant embryos serially in a fluid carrier in an upstream fluid conduit, said upstream fluid conduit having an inner diameter that is small enough to ensure that the directional orientation of the embryos is maintained and the embryos pass through the upstream fluid conduit serially;

(b) obtaining information regarding a plant embryo at a location in the upstream fluid conduit; and (c) selectively delivering the plant embryo to one of the at least two downstream fluid conduits according to the information by substantially aligning an end of the upstream fluid conduit with an end of one of the at least two downstream fluid conduits.

2. The method of claim 1 wherein step (c) produces a fluid-tight path comprising the upstream conduit and one of the at least two downstream fluid conduits.

3. The method of claim 1 wherein the upstream and downstream fluid conduits are aseptic so as to prevent contamination of the fluid and the plant embryos.

4. The method of claim 1 wherein flow of the carrier fluid in the upstream and downstream conduits is substantially nonturbulent.

5. A method for directing plant embryos from a first upstream fluid conduit to one of at least two downstream fluid conduits, the method comprising:

(a) transporting plant embryos serially in a fluid carrier in an upstream fluid conduit, said upstream fluid conduit having an inner diameter that is small enough to ensure that the directional orientation of the embryos is maintained and the embryos pass through the upstream fluid conduit serially;

(b) obtaining information regarding a plant embryo at a location in the upstream fluid conduit; and (c) selectively aligning a fluid chamber with the upstream conduit to receive the plant embryo and then aligning the fluid chamber with one of at least two downstream fluid conduits to direct the plant embryo thereto according to the information.

6. The method of claim 5 wherein the upstream and downstream fluid conduits and the fluid chamber are aseptic so as to prevent contamination of the fluid and the plant embryos.

7. The method of claim 5 wherein:

the information is an image of the plant embryo;

the method further comprises the steps of assigning the plant embryo to a first or second class; and producing a first or second signal corresponding to the class to which the plant embryo is assigned; and the fluid chamber is aligned (i) with a first downstream conduit in response to the first signal or (ii) with a second downstream conduit in response to the second signal.

8. A method for producing a desired spacing between spaced apart plant embryos, the method comprising:

(a) serially transporting plant embryos in a fluid stream in an upstream fluid conduit, said upstream fluid conduit having an inner diameter that is small enough to ensure that the directional orientation of the embryos is maintained and the embryos pass through the upstream fluid conduit serially;

(b) directing the stream of fluid to a first downstream fluid conduit;

(c) detecting a plant embryo in the fluid stream at a location in the upstream fluid conduit; and (d) directing the fluid stream to a second downstream conduit, then, after a predetermined time, directing the fluid stream to the first downstream conduit to produce the desired spacing.

9. The method of claim 8 wherein the fluid stream is directed to the first or second downstream conduit by substantially aligning an end of the upstream conduit with an end of the first or second downstream conduit, respectively.

10. The method of claim 9 wherein the fluid stream is directed to the first or second downstream conduit by producing a fluid-tight path comprising the upstream conduit and either the first or second downstream conduit, respectively.

11. The method of claim 8 wherein the upstream and downstream fluid conduits are aseptic so as to prevent contamination of the fluid and the plant embryos.

12. A method for producing a manufactured seed comprising a plant embryo comprising the steps of:
 (a) transporting plant embryos serially in a fluid carrier in an upstream fluid conduit said upstream fluid conduit having an inner diameter that is small enough to ensure that the directional orientation of the embryos is maintained and the embryos pass through the upstream fluid conduit serially;
 (b) obtaining information regarding an embryo at a location in the upstream fluid conduit;
 (c) delivering the embryo from the upstream fluid conduit to either a first or a second downstream fluid conduit by substantially aligning an end of the upstream fluid conduit with an end of either the first or the second downstream fluid conduit according to the information; and
 (d) producing a manufactured seed from the embryo.

* * * * *